(12) United States Patent
Townsend

(10) Patent No.: US 10,729,353 B2
(45) Date of Patent: Aug. 4, 2020

(54) ELECTRODE ARRAY FOR ELECTROENCEPHALOGRAMS

(71) Applicant: George Townsend, Sault Ste. Marie (CA)

(72) Inventor: George Townsend, Sault Ste. Marie (CA)

( * ) Notice: Subject to any disclaimer, the term of this patent is extended or adjusted under 35 U.S.C. 154(b) by 1001 days.

(21) Appl. No.: 15/191,748

(22) Filed: Jun. 24, 2016

(65) Prior Publication Data

US 2016/0374584 A1    Dec. 29, 2016

(30) Foreign Application Priority Data

Jun. 26, 2015 (CA) ...................................... 2895593

(51) Int. Cl.
*H03F 3/45* (2006.01)
*A61B 5/0478* (2006.01)
*A61B 5/04* (2006.01)

(52) U.S. Cl.
CPC ........ *A61B 5/0478* (2013.01); *A61B 5/04004* (2013.01); *A61B 2562/046* (2013.01)

(58) Field of Classification Search
CPC ........................................................ H03F 3/45
USPC ............................................... 330/69, 124 R
See application file for complete search history.

(56) References Cited

U.S. PATENT DOCUMENTS 8,059,103 B2*  11/2011  Geaghan ............... G06F 3/044
                                                      345/173
2015/0109007 A1   4/2015  Townsend

FOREIGN PATENT DOCUMENTS

CA          2864612 A1    10/2013
WO       2013142944 A1    10/2013

* cited by examiner

*Primary Examiner* — Henry Choe
(74) *Attorney, Agent, or Firm* — Withrow & Terranova, P.L.L.C.; Vincent K. Gustafson

(57) ABSTRACT

An electrode array for EEGs is described that includes a feedback amplifier driving one of the electrodes. Use of the feedback amplifier can eliminate the need to use precisely balanced resistors in a differential amplifier as well as allowing the elimination of a reference electrode and ground electrode.

10 Claims, 6 Drawing Sheets

ELECTRODE ARRAY FOR ELECTROENCEPHALOGRAMS

TECHNICAL FIELD

The current disclosure relates to electroencephalograms (EEGs) and in particular to electrodes used in capturing EEG signals.

BACKGROUND

EEG systems use electrodes connected to a scalp in order to detect small electrical signals. These small signals are generally amplified for further processing. Previous electrodes have utilized differential amplifiers for amplifying the desired signals. However, differential amplifiers require delicate balancing of the resistors used to achieve accurate differential amplification required to achieve a high common mode rejection ratio (CMR) of the system. Standard implementations, even those using delicately-balanced laser trimmed resistors, suffer from the inability to remain perfectly balanced over time and over varying operating conditions.

SUMMARY

In accordance with the present disclosure there is provided an electrode array comprising: a plurality of electrodes each for capturing an EEG signal; and a feedback amplifier providing the output signal based on a difference between ground and a combined average signal of an output signal of each of the plurality of electrodes.

BRIEF DESCRIPTION OF THE DRAWINGS

Further features and advantages of the present disclosure will become apparent from the following detailed description, taken in combination with the appended drawings, in which.

DETAILED DESCRIPTION

An active electrode array system is described that allows EEG signals to be captured from active electrodes without the use of additional electrodes for reference and ground signals. As described further, the active electrode array does not require a dedicated bias (i.e. ground) electrode nor a reference electrode. A feedback amplifier is used to force the common average of the output signals to zero, which as detailed further below, cancels out any common average signal of the outputs as well as cancelling out any common mode signal of the outputs.

Figure 1B:
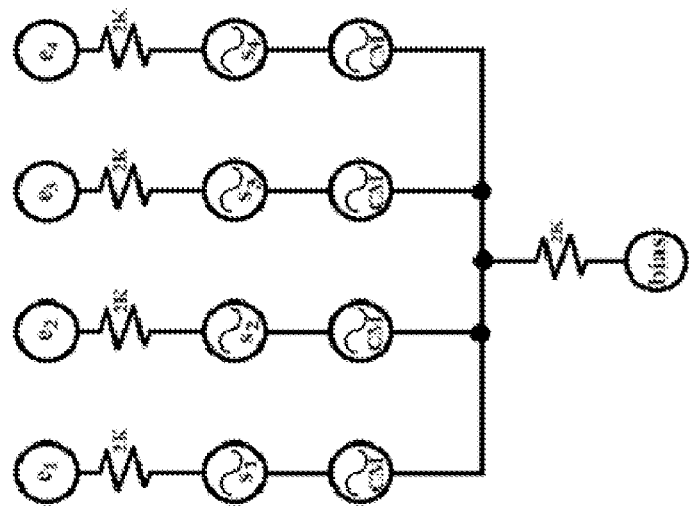
FIG. 1B depicts an equivalent model of the scalp electrodes of FIG. 1A.
Figure 1A:
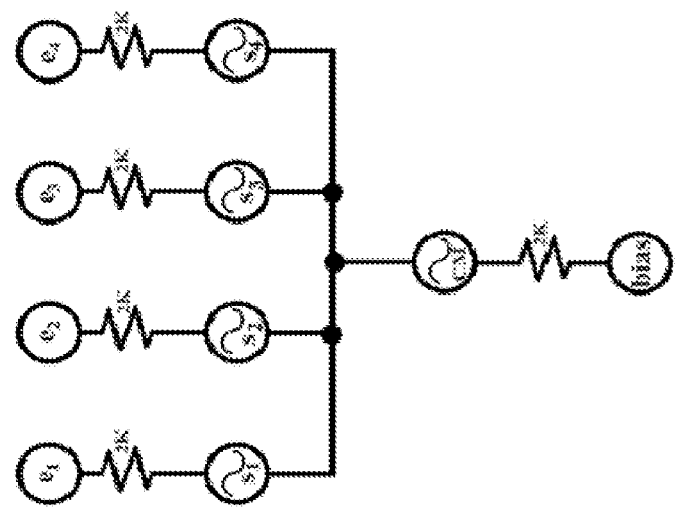
FIG. 1A depicts a model of scalp electrodes.

The active electrode array system is presented below in evolutionary stages to make the operation clearer. FIGS. 1A and 1B depict traditional models of scalp electrodes. The models of FIGS. 1A and 1B use no reference electrode but include a bias electrode (often commonly referred to as a ground electrode). The underlying signals of interest on the scalp are depicted as signals $s_1$, $s_2$, $s_3$, and $s_4$. A common mode signal CM with respect to a bias electrode is added to these signals. The scalp electrodes used to connect to scalp locations for capturing the signals $s_1$, $s_2$, $s_3$, and $s_4$ are modeled as 2-kilohm resistors to account for the electrode-gel-skin junction. A DC offset due to electrochemistry is not included in the model since the DC offset is unnecessary to describe the operation of the array. The model depicted in FIG. 1A provides a basis used in further analysis presented below. The signals acquired by the electrodes with respect to the bias electrode are then $e_1$, $e_2$, $e_3$ and $e_4$, where $e_n = s_n + CM$. Note that the circles in the diagrams with a sine symbol represent voltage sources in the analysis while those without represent scalp electrodes. The 2-kilohm resistances represent the impedance of each scalp electrode.

FIG. 1A depicts a model of scalp electrodes in which any one of the signal electrodes may be treated as a reference electrode and all acquired signals contain a common mode signal CM.

FIG. 1B is an equivalent model as FIG. 1A, however the common mode signal CM is depicted as individual signals for each of the signals for compatibility with further discussions in the variations which follow below.

In a traditional electrode array, a reference electrode and a bias electrode would be present and the acquired signals would be voltages with respect to the bias electrode that would then be subtracted from a reference voltage taken from the reference electrode with respect to the bias electrode. This subtraction requires differential amplifiers. Some electrode arrays may eliminate the reference electrode by taking a common average (CAR) of all of the signals with respect to the bias electrode and using the CAR in place of the reference voltage.

The active electrode array described herein does not require differential amplifiers for each channel. Instead the array sets the voltage on the bias electrode such that the CAR of all the acquired signals with respect to the amplifier's ground is zero at all times. This will also account for any DC offsets due to electrochemistry. The active electrode array includes a feedback operational amplifier in which the non-inverting input is grounded, and the output controls the active electrode array to maintain a virtual ground at the inverting input of the feedback amplifier. This mechanism is used to ensure that all the signals of interest are always with respect to the amplifier's ground eliminating the requirement for differential amplification.

Figure 2:
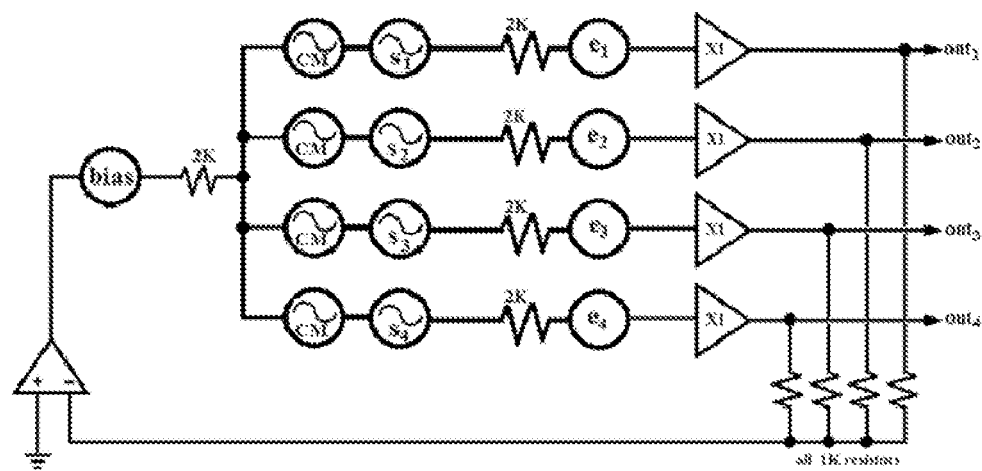
FIG. 2 depicts an embodiment of an active electrode array.

FIG. 2 depicts an embodiment of an active electrode array. The embodiment depicted in FIG. 2 includes a bias electrode. As described further, the bias electrode may be omitted; however is included in the embodiment of FIG. 2 in order to clarify the genesis of the active electrode array from the models depicted in FIGS. 1A and 1B. The array comprises a unity gain amplifier per electrode, although other gains are possible (when a reference electrode is used), and a feedback amplifier. The feedback amplifier is used to set the bias voltage equal to whatever value is required to produce a CAR of zero with respect to the system ground. There is no critical balancing of resistors required anywhere in the circuit to ensure that the common mode signal is completely rejected. The CM signal(s) have been maintained in the depiction of FIG. 2 and in the analysis in an attempt to model a common mode signal, however the operation of the active electrode array effectively eliminates the common mode signal.

As depicted in FIG. 2, the bias electrode is driven by a signal from the feedback op-amp whose output will be whatever voltage is required to maintain the CAR of the acquired signals ($e_1$ through $e_4$) at zero relative to the ground connected to the non-inverting input of the feedback op-amp. The CAR is provided to the inverting input of the feedback op-amp by connecting the output of the amplifiers associated with electrodes to the inverting input through respective resistors, such as 1K resistors as depicted, although the particular resistance used is not critical. As depicted in FIG. 2, the feedback amplifier forces the CAR of the acquired signals $e_1$ through $e_4$ to be zero by adjusting the bias electrode. An analysis of this behavior shows that the acquired signals will be equal to the underlying signals $s_1$ through $s_4$ with the CAR of the underlying signals and the common mode signal CM both subtracted out.

Since circuit depicted in FIG. 2 forces the CAR of the acquired voltages on electrodes $e_1$ through $e_4$ to be zero, the sum of these voltages must be zero. Although the precision of the resistors will affect how accurate the generated CAR is, their balance will not affect the common mode signal, and therefore the balance of these resistors is not critical. Although not necessary, it is assumed that these resistors are balanced. The extremely high input impedances of op-amps (10 G ohms) ensures that virtually no current will flow from the output of the feedback amplifier through the 2K resistances in the model. Therefore the voltage drop across these resistors may be ignored. Then each acquired electrode voltage "$e_n$" with respect to the system ground will be the output of the feedback amplifier plus the common mode signal CM plus the underlying signal $s_n$ represented at the associated electrode.

It is noted that there is a distinction between the CAR of the acquired signals ($e_1$ through $e_4$) at the negative input to the feedback amplifier and the CAR of the underlying signals ($s_1$ through $s_4$). $CAR_s$ is used to denote the latter and $CAR_e$ is used to denote the former. From the above, there are a number of equations and unknowns:

Let x be the voltage at the output of the feedback amplifier. Then:

$$x+CM+s_1=e_1 \quad (1)$$

$$x+CM+s_2=e_2 \quad (2)$$

$$x+CM+s_3=e_3 \quad (3)$$

$$x+CM+s_4=e_4 \quad (4)$$

$$CAR_e=(e_1+e_2+e_3+e_4)/4=0 \quad (5)$$

Substituting (1) through (4) into (5) gives:

$$(x+CM+s_1+x+CM+s_2+x+CM+s_3+x+CM+s_4)/4=0 \quad (6)$$

$$x+CM+(s_1+s_2+s_3+s_4)/4=0 \quad (7)$$

$$x=-CM-CAR_s \quad (8)$$

This may now be substituted back into each equation for the acquired signal voltages in terms of each underlying signal voltage "$s_n$" and the CAR of these signals, $CAR_s$ as follows:

$$e_1=x+CM+s_1=-CM-CAR_s+CM+s_1=s_1-CARs \quad (9)$$

Similarly, $$e_2=s_2-CAR_s \quad (10)$$

$$e_3=s_3-CAR_s \quad (11)$$

$$s_4=s_4-CAR_s \quad (12)$$

In other words, every acquired signal $e_n$ is the corresponding underlying signal $s_n$ with the CAR of the underlying signals and the common mode signal CM subtracted out.

If the balance of the 1 k CAR resistors is uneven, the CAR of the underlying signals will not be accurate, however the sum of each instance of the common mode noise, unequally weighted, will still add up to the full value of CM and therefore CM will remain fully rejected in any case. In other words, for any four weights $w_1$ through $w_4$ used in an unevenly balanced CAR, the sum of $w_1CM+w_2CM+w_3CM+w_4CM$ will be equal to $(w_1+w_2+w_3+w_4)$ CM. Since the sum of any set of weights is by definition 1, this is equal at all times to CM.

Figure 3:
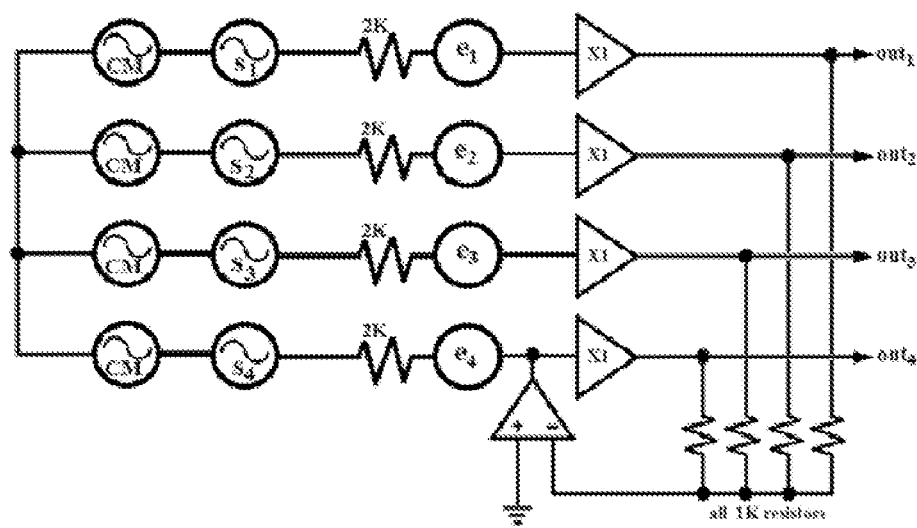
FIG. 3 depicts a further embodiment of an active electrode array.

FIG. 3 depicts a further embodiment of an active electrode array. The array depicted in FIG. 3 eliminates the dedicated bias electrode altogether, and in its place any one of the signal electrodes may be selected. It will be shown that the output "x" of the feedback amplifier in this case is equal to the underlying source voltage $s_n$ at the selected electrode less the CAR of the underlying signals and the common mode signal CM. Therefore, any one of the signal electrodes may be chosen to simultaneously act as the bias electrode. The novel result is an array that requires N electrodes to acquire N signals of interest. Neither a dedicated bias, nor a reference electrode is present in the active electrode array depicted in FIG. 3. An analysis confirms that even though electrode $e_4$ is driven by the feedback amplifier, the output of the feedback amplifier is equal to the underlying signal $s_4$ with the common average of the underlying signals and the common mode signal CM both subtracted out. That general relationship between $e_n$ and $s_n$ is maintained for all electrodes. All final output signals are with respect to the circuit ground.

Figure 4:
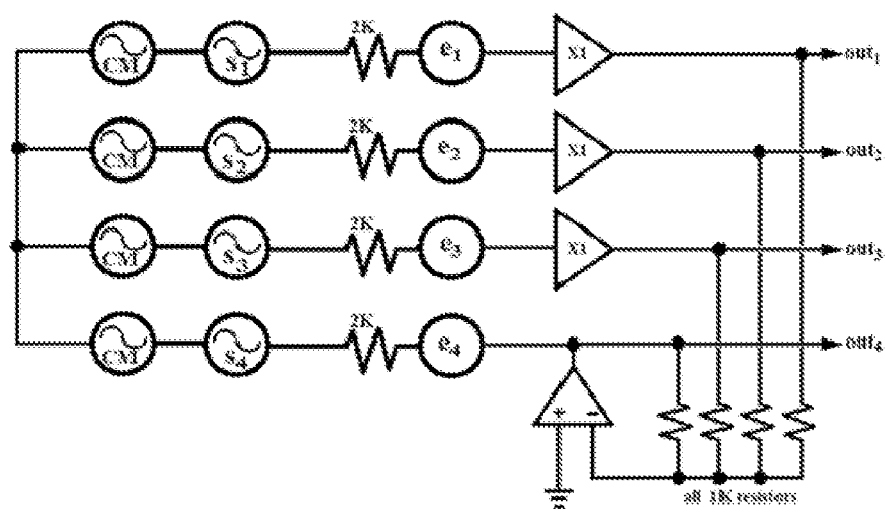
FIG. 4 depicts a further embodiment of an active electrode array.

As depicted in FIG. 3, $e_4$ is driven by the feedback amplifier. Note that the unity gain amplifier on $e_4$'s channel is now redundant and may be removed, for example by replacing it with a wire as depicted in FIG. 4, without affecting the operation of the array. The analysis now requires the inclusion of paths down through a virtual common mode source voltage and back up to the other electrodes resulting in $-CM+CM=0$. In other words, any common mode signal will be completely rejected. The analysis is then as follows:

$$x=e_4 \quad (13)$$

$$CAR_e=(e_1+e_2+e_3+e_4)/4=0 \quad (14)$$

$$e_1=x-s_4-CM+CM+s_1=e_4-s_4+s_1 \quad (15)$$

Similarly, $$e_2=e_4-s_4+s_2 \quad (16)$$

$$e_3=e_4-s_4+s_3 \quad (17)$$

Therefore:

$$(e_4-s_4+s_1+e_4-s_4+s_2+e_4-s_4+s_3+e_4)/4=0 \quad (18)$$

$$(4e_4-4s_4+s_1+s_2+s_3+s_4)/4=0 \quad (19)$$

$$e_4-s_4+CAR_s=0 \quad (20)$$

$$e_4=s_4-CAR_s \quad (21)$$

This expression for $e_4$ may now be substituted into the other equations to yield:

$$e_1=s_4-CAR_s-s_4+s_1=s_1-CAR_s \quad (22)$$

Similarly, $$e_2 = s_2 - CAR_s \quad (23)$$

$$e_3 = s_3 - CAR_s \quad (24)$$

In other words, all four acquired signals in each case are the corresponding underlying signal minus the CAR of the underlying signals.

The common mode rejection of the completed circuit shown in FIG. 4 is sufficiently high that no 60 Hz filter is required. Interestingly, it requires only a single op-amp per channel to implement.

FIG. 4 depicts an embodiment in which the redundant operational amplifier included in the previous figure has been removed.

Figure 5:
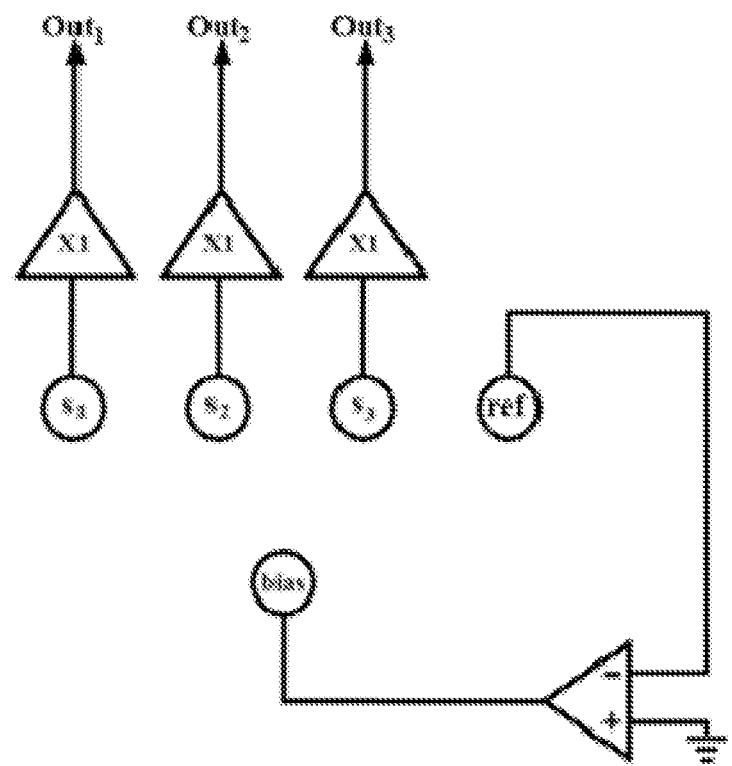
FIG. 5 depicts a further electrode array utilizing a feedback amplifier.

FIG. 5 depicts a further electrode array utilizing a feedback amplifier. Although described above as eliminating the need for reference and bias electrodes, the feedback amplifier may be incorporated into a more conventional array with a dedicated bias and reference electrode. In such an array, no resistors are required, and the output voltages are all with respect to the system ground and represent the difference between each signal electrode and the reference electrode. Although this configuration, shown in FIG. 5, maintains the traditional bias and reference electrodes, no balancing resistors and no differential amplifiers are required. Therefore, the common mode rejection ratio may be extremely high. This implementation allows for direct measurement of the CMR (Common Mode Rejection), however the nature of the implementation does not take full advantage of the array and so the CMR is not ideal. Despite that, simulations show the CMR to be on the order of −147 dB, and initial real-world test have shown a CMR of −107 dB. Similar analysis to that given earlier shows each extracted signal to be the difference between the underlying signal and the reference electrode, in both cases taken with respect to the system ground. In this configuration the amplifier connected to the reference electrode should be physically located at the reference electrode rather than at the bias electrode.

The above has described an active electrode array in which the amplifier associated with a particular electrode is physically located at that electrode location. Any of the configurations discussed above may be run with the electronics located at the electrodes, or centrally at a distance from the scalp electrodes in which case the configuration may be considered a passive electrode version of the associated active configuration.

From the above, an electrode array may be provided that does not contain the traditional differential amplifiers that would normally be required in an EEG system. Such amplifiers require delicate balancing of the resistors used to achieve accurate differential amplification to subsequently achieve a high CMR of the system. The electrode array described here may reject the common mode signal without the use of traditional differential amplifiers. Standard implementations (even those using delicately-balanced laser trimmed resistors) suffer from the inability to remain perfectly balanced over time and over varying operating conditions. The electrode array presented above does not suffer from such problems, resulting in reliable, consistent rejection of the common mode signal.

The electrode array described above may use only signal electrodes. For example, an eight channel system which acquires eight signals of interest from the scalp can be implemented using only eight electrodes in total. No reference electrode is required, nor is a ground (sometimes called a bias) electrode required. This arrangement can provide a very high common mode rejection (CMR). The implementation does not require differential amplifiers thereby eliminating the need for critical balancing of resistors to achieve high CMR. The outputs of the system are with respect to the circuit ground and represent the signals of interest with the common average (CAR) and common mode noise removed. Variations of the electrode array which do include a bias and/or reference electrode may be used in situations where removal of the CAR is not desired. Such arrays still do not require differential amplifiers. The signals from the array are sufficiently clean and free of 50/60 Hz noise that no notch filter is required.

Furthermore, the unique design allows greater than unity amplification, right at the electrodes. Normally, active electrodes use unity gain amplifiers since this is the only way to have a precise gain in order that differential amplification in the system will work correctly. In the design of the described electrode array, inexact gain only affects the accuracy of the CAR but does not affect the CMR of the system. Therefore this system allows for cleaner signals than would normally be expected by allowing higher gains right at the electrode. The limiting factor on the gain is determined by the battery voltage and the DC offset produced by the skin-gel-electrode junction. As long as the gain does not amplify this DC offset to reach either power supply rail, it is acceptable. Accounting for a typical DC offset of 100 mV and a typical supply voltage of +/−1.5 V, gains of up to 15 may be acceptable.

Figure 6:
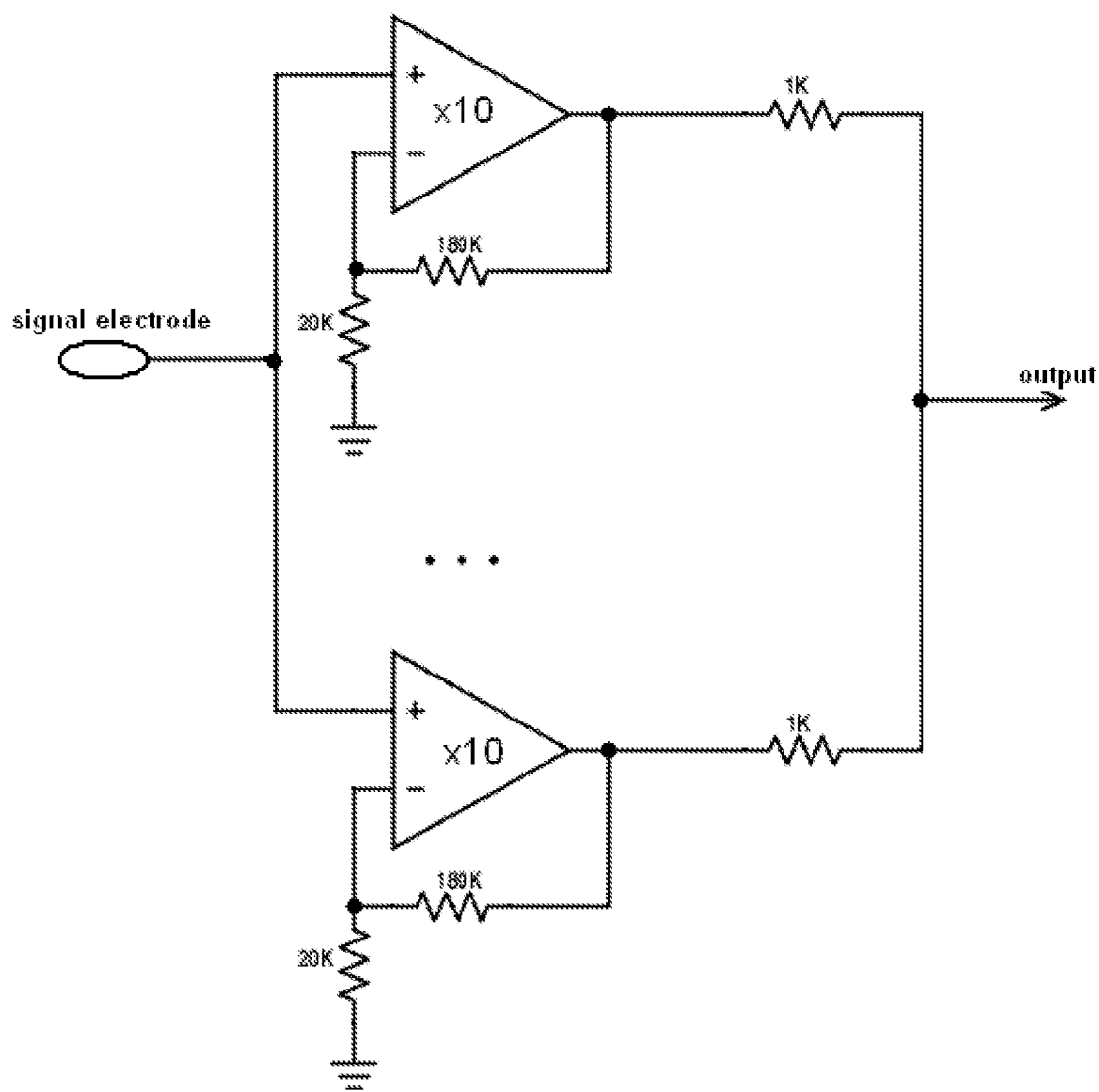
FIG. 6 depicts an electrode arrangement.

FIG. 6 depicts an electrode arrangement. Given the small size of modern op-amps, it is possible to place several amps on an active electrode in order to reduce the noise produced within each amplifier by averaging their outputs. This reduces internally generated noise by a factor of the square root of the number of amplifiers averaged together. So for example, an increase in the SNR ration of the system by a factor of 3 may be achieved by paralleling the outputs of nine op-amps together on the electrode. This technique in conjunction with the use of greater than unity gain amplifiers produces significantly improved signals over traditional approaches. Furthermore, in the CAR version of the implementation, the CMR is actually enhanced since adding the gain at this point in the circuit only adds gain to the signals of interest and does not increase the common mode signal. For example, a gain of 10 on each signal amplifier will enhance the CMR by −20 dB.

The invention claimed is:
1. An electrode array comprising:
  a first electrode arranged for capturing a first electroencephalogram (EEG) signal and providing a corresponding first output signal;
  a second electrode arranged for capturing a second EEG signal and providing a corresponding second output signal;
  a third electrode arranged for capturing a third EEG signal and providing a corresponding third output signal;
  a fourth electrode arranged for capturing a fourth EEG signal and providing a corresponding fourth output signal; and
  a feedback amplifier providing an amplifier output signal based on a difference between: ground; and
    a combined average signal which is an average of multiple signals comprising:
      the first output signal;
      the second output signal;
      the third output signal; and
      the fourth output signal.

2. The electrode array of claim 1, wherein the amplifier output signal of the feedback amplifier drives a selected one of the first to fourth electrodes.

3. The electrode array of claim 2, further comprising a plurality of amplifiers each associated with respective ones of the first to fourth electrode other than the selected one of the first to fourth electrodes.

4. The electrode array of claim 3, wherein each amplifier of the plurality of amplifiers is a unity gain amplifier.

5. The electrode array of claim 3, wherein each amplifier of the plurality of amplifiers is a greater than unity gain amplifier.

6. The electrode array of claim 1, wherein one or more of the first to fourth electrodes is an active electrode.

7. The electrode array of claim 1, wherein one or more of the first to fourth electrodes is a passive electrode.

8. The electrode array of claim 1, wherein at least one electrode of the first to fourth electrodes is associated with a plurality of amplifiers, and an averaged output of the plurality of amplifiers provides an output for the associated electrode.

9. The electrode array of claim 1, wherein the combined average signal is generated using:
   a first resistor having a first terminal and a second terminal, the first terminal coupled to the first electrode outputting the first output signal and the second terminal connected to a common connection point providing the combined average signal;
   a second resistor having a first terminal and a second terminal, the first terminal coupled to the second electrode outputting the second output signal and the second terminal connected to the common connection point providing the combined average signal;
   a third resistor having a first terminal and a second terminal, the first terminal coupled to the third electrode outputting the third output signal and the second terminal connected to the common connection point providing the combined average signal; and
   a fourth resistor having a first terminal and a second terminal, the first terminal coupled to the fourth electrode outputting the fourth output signal and the second terminal connected to the common connection point providing the combined average signal.

10. The electrode array of claim 1, further comprising:
   one or more additional electrodes each arranged for capturing a respective EEG signal and providing a respective output signal,
   wherein the combined average signal is an average of:
      the first output signal;
      the second output signal;
      the third output signal;
      the fourth output signal; and
      each of the respective output signals of the one or more additional electrodes.

* * * * *